United States Patent
Close et al.

(10) Patent No.: US 8,722,946 B2
(45) Date of Patent: May 13, 2014

(54) METHOD FOR AVOIDING THE GENERATION OF BY-PRODUCTS DURING THE PRODUCTION OF HALOALKANE COMPOUNDS

(75) Inventors: Joshua Close, Blasdell, NY (US); Haiyou Wang, Amherst, NY (US); Hsueh Sung Tung, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 62 days.

(21) Appl. No.: 13/481,111

(22) Filed: May 25, 2012

(65) Prior Publication Data

US 2012/0310020 A1    Dec. 6, 2012

Related U.S. Application Data

(60) Provisional application No. 61/492,918, filed on Jun. 3, 2011.

(51) Int. Cl.
  *C07C 17/275* (2006.01)
(52) U.S. Cl.
  USPC .......................................... 570/257; 570/261
(58) Field of Classification Search
  USPC .................................................. 570/171, 261
  See application file for complete search history.

(56) References Cited

U.S. PATENT DOCUMENTS

| | | | |
|---|---|---|---|
| 5,902,914 A | 5/1999 | Rygas et al. | |
| 6,187,978 B1 * | 2/2001 | Rygas et al. | 570/257 |
| 6,193,221 B1 * | 2/2001 | Sherman | 261/87 |
| 6,313,360 B1 | 11/2001 | Wilson et al. | |
| 7,094,936 B1 | 8/2006 | Owens et al. | |
| 7,102,041 B2 | 9/2006 | Tung | |
| 2004/0225166 A1 * | 11/2004 | Wilson et al. | 570/171 |
| 2008/0091053 A1 | 4/2008 | Tung et al. | |
| 2009/0216055 A1 * | 8/2009 | Wilson et al. | 570/219 |

FOREIGN PATENT DOCUMENTS

| | | |
|---|---|---|
| EP | 729932 A1 | 9/1996 |
| JP | 2000-086545 A | 3/2000 |

* cited by examiner

*Primary Examiner* — Jafar Parsa
*Assistant Examiner* — Medhanit Bahta
(74) *Attorney, Agent, or Firm* — Bruce O. Bradford

(57) ABSTRACT

Disclosed is a process for the manufacture of haloalkane compounds, and more particularly, to an improved process for the manufacture of the compound 1,1,1,3,3-pentachloropropane (HCC-240fa), which mitigates the formation of by-products. The present invention is also useful in the manufacture of other haloalkane compounds such as HCC-250 and HCC-360. One embodiment of the process comprises a method and system for avoiding the formation of polyvinyl chloride during the production of HCC-240fa from $CCl_4$, in which vinyl chloride (VCM) is fed into a reactor as a vapor instead of as a liquid, using a diffusing device to further increase the contact surface between VCM vapor and $CCl_4$.

19 Claims, No Drawings

METHOD FOR AVOIDING THE GENERATION OF BY-PRODUCTS DURING THE PRODUCTION OF HALOALKANE COMPOUNDS

CROSS-REFERENCE TO RELATED APPLICATION

This application claims domestic priority to commonly owned, U.S. Provisional Patent Application Ser. No. 61/492,918, filed Jun. 3, 2011, the disclosure of which is hereby incorporated herein by reference.

FIELD OF THE INVENTION

The present invention relates to a process for the manufacture of haloalkane compounds, and more particularly, to an improved process for the manufacture of 1,1,1,3,3-pentachloro-propane (HCC-240fa). The present invention is also useful in the manufacturing of other haloalkane compounds such as HCC-250 and HCC-360.

BACKGROUND OF THE INVENTION

The compound 1,1,1,3,3-pentachloropropane (HCC-240fa) is a raw material for producing 1,1,1,3,3-pentafluoropropane (HFC-245fa), which is a non-ozone depleting chemical and can be used as blowing agent, energy transfer medium, and so on. Addition reactions for preparing useful haloalkanes, such as HCC-240fa, are known in the art. For example, U.S. Pat. No. 6,313,360 teaches a process for producing HCC-240fa by reacting carbon tetrachloride ($CCl_4$) and vinyl chloride monomer ($H_2C=CHCl$ or VCM) in the presence of a catalyst mixture comprising organophosphate, e.g., tributylphosphate (TBP), metallic iron and ferric chloride under conditions sufficient to produce a product mixture containing HCC-240fa. The 240fa product is then recovered by separating it from reactants, catalyst and by-products. See also, U.S. Pat. Nos. 5,902,914, 6,187,978, and 7,102,041. See also, U.S. Patent Publication No. 2008/0091053, and EP Patent Pub. No. 729932. The disclosures of all of these references are hereby incorporated herein by reference.

VCM is a liquefied gas and a precursor to polyvinyl chloride (PVC), a potential undesired solid by-product in the production of HCC-240fa. Indeed, it was observed that the addition of liquid VCM to a reactor containing $CCl_4$, TBP, and $Fe^0$ resulted in a significant exotherm and the formation of excessive amount of solid material characteristic of PVC. The detrimental impacts of the formation of PVC include:
(1) yield loss,
(2) difficulty in heat management, and
(3) reduced catalyst activity (iron particles may be encapsulated by PVC).
Therefore, the present applicants have come to appreciate the need for means by which the formation of PVC in HCC-240fa production process can be avoided. The present invention solves this problem.

SUMMARY OF THE INVENTION

The present invention relates to a process for the manufacture of haloalkane compounds, and more particularly, to an improved process for the manufacture of the compound 1,1,1,3,3-pentachloropropane (HCC-240fa). The present invention is also useful in the manufacturing processes for making other haloalkane compounds such as HCC-250 and HCC-360.

In one embodiment, the present invention is directed to an improved process for making HCC-240fa. The present invention provides a method and system for avoiding the formation of polyvinyl chloride during the production of HCC-240fa, in which the VCM is fed into reactor as a vapor instead of a liquid through a diffusing device, such as a dip tube, a sponge type gas diffuser, or the like, to further increase the contact surface between VCM vapor and $CCl_4$.

In one embodiment, VCM vapor is fed into a reactor precharged with $CCl_4$, TBP and iron powder through a dip tube. In this manner, the contact surface between the VCM vapor and the $CCl_4$ is increased, which improves the reactivity. In another embodiment, the VCM vapor is fed into a reactor precharged with $CCl_4$, TBP and iron powder through a sponge type gas diffuser to further increase the contact surface between VCM vapor and $CCl_4$. The gas diffuser can be made of glass or any metals that are compatible with the reaction mixture.

In one aspect, the invention provides an improved process for manufacturing HCC-240fa, which comprises:
(a) providing a continuous $CCl_4$ liquid stream and a continuous VCM vapor stream;
(b) producing a product stream in a reactor by reacting carbon tetrachloride and vinyl chloride in the presence of a catalyst mixture consisting of iron metal and tributylphosphate under conditions sufficient to produce HCC-240fa, and
(c) recovering HCC-240fa from said product stream of step (b).

In accordance with another aspect of the invention a system for producing HCC-240fa is provided. The system comprises:
(1) A feed delivery apparatus wherein a continuous $CCl_4$ liquid stream and a continuous VCM vapor stream are provided,
(2) A reactor wherein carbon tetrachloride and vinyl chloride in the presence of a catalyst mixture consisting of iron metal and tributylphosphate are reacted under conditions sufficient to produce HCC-240fa product stream, and
(3) One or multiple flash-distilling columns wherein HCC-240fa can be separated and purified as a final product.

The present invention is also useful in the processes for making other haloalkane compounds such as HCC-250 and HCC-360:
(1) HCC-250 may be made from $CCl_4$ and ethylene as per the following reaction:

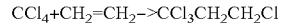

In this case, the undesired by-products which are reduced or eliminated by the processing conditions taught herein are polyethylene.

(2) HCC-360 may be made from $CCl_4$ and 2-chloropropene as per the following reaction:

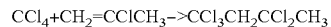

In this case, the undesired by-products which are reduced or eliminated by the processing conditions taught herein are poly(2-chloropropene).

It should be appreciated by those persons having ordinary skill in the art(s) to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure.

It is to be understood that both the foregoing general description and the following detailed description are exemplary and explanatory only and are not restrictive of the invention as claimed. Other embodiments will be apparent to those skilled in the art from consideration of the specification and practice of the invention disclosed herein.

DETAILED DESCRIPTION OF THE INVENTION

The reaction of carbon tetrachloride and vinyl chloride is carried out in a glass-lined reactor, which is equipped with an agitator. In the inventive process, $CCl_4$ liquid and VCM vapor are continuously fed into reactor at desired ratio through a diffusing device such as a dip tube, or more preferably, through a sponge type gas diffuser. By doing so, the contact surface between VCM vapor and $CCl_4$ liquid is increased, which improves the reactivity. The reaction of vinyl chloride and carbon tetrachloride to form HCC-240fa is preferably initiated utilizing iron powder as the catalyst and an organophosphate compound such as tributylphosphate as the co-catalyst. While batch processing can be used for the reactions of the present invention, it is preferred that continuous manufacturing processing is used herein.

The iron powder useful in this invention is preferably a fine powder of pure metallic iron, preferably with a particle size smaller than 325 mesh, but other mesh sizes can be used if so desired. Iron powder and TBP can be added into reactor periodically or continuously, but the continuous mode is preferred. Iron powder may be added to the reactor by any means, but powder slurry in carbon tetrachloride, in TBP, or in the mixture of both is preferred. While iron powder is preferred, any iron object can be used, such as iron balls, iron wire, iron shavings, and the like.

The co-catalyst TBP is a chelating agent and also serves as solvent to help dissolve the solid catalyst. The mole ratio of iron powder to tributylphosphate may be about 0.05:1 to about 500.0:1, preferably about 1.0:1 to about 100.0:1, and more preferably about 1.5:1 to about 10:1. The preferred concentration of the catalyst in the reaction mixture is from about 0.001 to about 20 weight percent, preferably from about 0.01 to about 10 weight percent, and more preferably from about 0.1 to about 5 weight percent. Additional organophosphate compounds useful herein as co-catalysts include the following: triphenylphosphate, tributylphosphate, triethylphosphate, trimethyl-phosphate, tripropylphosphate or any other similar organophosphate compound, and mixtures of two or more of these compounds.

Generally, the mole ratio of $CCl_4$ to VCM is from about 0.02:1 to about 50:1. Preferably, the ratio is from about 0.1:1 to about 4.0:1 and more preferably from about 1:1 to about 3:1. The reaction can be operated at a temperature ranged from about 40° C. to about 180° C., preferably from about 85° C. to about 150° C., with agitation. The reaction temperature and catalytic activity inherently determine the reactor pressure, which is preferably from 30 psia to 60 psia. The reaction is preferably carried out at a residence time of from about 0.01 hours to about 24 hours, preferably from about 1 hour to about 12 hours. The reaction conditions are selected for high VCM efficiency, high HCC-240fa yield, and low by-products production.

In continuous operation, reactor contents are continually drawn through a tube immersed into liquid. After going through a filter where iron particles are trapped, reactor effluent stream is flash-distilled to remove a "top" stream including unreacted $CCl_4$ and VCM (if any) feed materials and the HCC-240 reaction product, while the catalyst/co-catalyst mixture remains.

The distillation may be performed in one or more distillation columns, which are well known in the art. Preferably, the flash-distillation is conducted in two steps: first, flash-distillation is conducted at a temperature less than the reaction temperature under a pressure, preferably under vacuum, to remove any unreacted $CCl_4$ and/or VCM, followed by another vacuum flash-distillation at a lower pressure to remove the HCC-240fa reaction product. The "bottoms" stream is recycled back to the reactor. The distilled, unreacted $CCl_4$ and VCM may be recycled back to the reactor. Periodical purges may be applied to avoid accumulation of heavy by-products such as HCC-470 isomers in the catalyst recycle stream.

In certain embodiments, a later step of the process further provides for the purification of the crude product by distillation. Fractional vacuum distillation is carried out at about 5 to about 200 mm Hg and a temperature of about 50° C. to about 150° C. to recover the product. It has been discovered that when this purification step is carried out in the presence of an organophosphate compound such as tributylphosphate or other metal chelating compound, the distillation yield of purified product is significantly improved.

While not wishing to be bound by any particular theory, it is believed that the tributylphosphate acts to prevent the decomposition of the HCC-240fa product. Thus, in a preferred embodiment, the purification step includes the addition of an amount of a metal chelating compound sufficient to improve the HCC-240fa product yield. Preferably, 5 weight percent of tributylphosphate is used.

If desired, the iron catalysts used in the production of the haloalkane compounds herein may be captured and recycled by the use of an electromagnetic separation unit (EMSU). When energized, the EMSU functions to remove the iron particles from the reactor effluent; when de-energized, the iron particles captured by the EMSU can be flushed back into the reactor for re-use in the continued production of the desired haloalkane compounds, such as HCC-240fa.

The following non-limiting examples serve to further illustrate the present invention.

EXAMPLE 1

136 g Tributylphosphate and 300 g of iron powder (mesh 325) were added to 41 lbs of carbon tetrachloride in a nitrogen purged, 5 gallon, glass lined, jacketed reactor. Using low pressure steam, the mixture was brought to a temperature of 100° C., venting non-condensables during warm-up. At temperature, liquid vinyl chloride was injected into the liquid mixture utilizing the reactor dip pipe. Upon introduction of liquid vinyl chloride, an unusually large exotherm was observed, causing the temperature of the reactor to quickly approach 125° C. before cooling water was established and the temperature was corrected to 100° C. The reaction was allowed to proceed until 8.3 lbs of vinyl chloride was added to the reactor. Following the reaction, the vessel was cleaned, yielding an amount of solids (i.e., a mixture of Fe & PVC) in excess of the weight of the iron powder that was added to start the reaction.

EXAMPLE 2

Reactor effluent, containing iron powder, was drawn through a filtration unit capable of removing solid particles prior to processing the organic stream. After several days, the filter became saturated with solids and was removed for clean-out. Solids were retrieved and analyzed with ICP and CHN. Analysis suggested that the solid sample was primarily composed of organics and iron. Furthermore, CHN elemental analysis revealed that the organic portion of the solid sample is characteristic of polyvinyl chloride.

EXAMPLE 3

The reaction given in Example 1 was repeated with the exception of the liquid vinyl chloride feed. Here, vapor vinyl chloride was bubbled into the liquid reaction mixture at a temperature of 100° C. Unlike the prior reaction that utilized the liquid form of vinyl chloride, the exotherm upon inject was much more mild. The temperature in the reactor only experienced a 1° C. to 2° C. change and was easily controlled without the need of cooling water.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A process for the manufacture of haloalkane compounds comprising reacting carbon tetrachloride and an alkene wherein poly(alkene) by-products are minimized during the reaction by the use of a diffusing device with an iron catalyst and one or more organo-phosphate compounds as a co-catalyst;
   wherein the alkene is selected from the group consisting of vinyl chloride, ethylene and 2-chloropropene; and
   wherein the haloalkane compounds are selected from the group consisting of HCC-240fa, HCC-250 and HCC-360; and wherein the diffusing device increases the contact surface between the reactants.

2. The process of claim 1, wherein the iron catalyst has a form selected from the group consisting of iron powder, iron balls, iron wire, iron shavings, and mixtures thereof.

3. The process of claim 2, wherein the iron powder comprises a fine powder of pure metallic iron.

4. The process of claim 3, wherein the iron powder has a particle size smaller than 325 mesh.

5. The process of claim 3, wherein the iron powder is added to the reactor by powder slurry in carbon tetrachloride.

6. The process of claim 3, wherein the iron powder is added to the reactor by powder slurry in the organophosphate.

7. The process of claim 3, wherein the iron powder is added to the reactor by powder slurry in a mixture of $CCl_4$ and the organophosphate.

8. The process of claim 1, wherein the organophosphate co-catalyst is selected from the group consisting of triphenylphosphate, tributylphosphate, trimethyl-phosphate, triethylphosphate, tripropylphosphate, and mixtures of two or more of these.

9. The process of claim 1, which is conducted as a continuous operation.

10. The process of claim 1, which is conducted as a batch operation.

11. The process of claim 1, wherein the diffusing device comprises a dip tube.

12. The process of claim 1, wherein the diffusing device comprises a sponge type gas diffuser.

13. An improved process for manufacturing HCC-240fa, which comprises:
    (a) providing a continuous $CCl_4$ liquid stream and a continuous VCM vapor stream;
    (b) producing a product stream in a reactor by reacting carbon tetrachloride and vinyl chloride in the presence of a catalyst mixture consisting of iron metal and tributylphosphate under conditions sufficient to produce HCC-240fa and not produce significant amounts of PVC by the use of a diffusing device, wherein the diffusing device increases the contact surface between the reactants; and
    (c) recovering HCC-240fa from said product stream of step (b).

14. The process of claim 13, wherein the VCM vapor is fed into a reactor precharged with $CCl_4$, tributylphosphate and iron powder through a dip tube.

15. The process of claim 13, wherein the VCM vapor is fed into a reactor precharged with $CCl_4$, tributylphosphate and iron powder through a sponge type gas diffuser.

16. The process of claim 13, wherein the iron powder has a particle size smaller than 325 mesh.

17. The process of claim 13, wherein the iron powder is added to the reactor by powder slurry in carbon tetrachloride.

18. The process of claim 13, wherein the iron powder is added to the reactor by powder slurry in the tributylphosphate.

19. The process of claim 13, wherein the iron powder is added to the reactor by powder slurry in a mixture of $CCl_4$ and the tributylphosphate.

* * * * *